(12) United States Patent
Masere

(10) Patent No.: US 9,447,002 B2
(45) Date of Patent: *Sep. 20, 2016

(54) 7-ACETYLENO QUINONE METHIDE DERIVATIVES AND THEIR APPLICATION AS VINYLIC POLYMERIZATION RETARDERS

(71) Applicant: NALCO COMPANY, Naperville, IL (US)

(72) Inventor: Jonathan Masere, Pearland, TX (US)

(73) Assignee: NALCO Company, Naperville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/527,495

(22) Filed: Oct. 29, 2014

(65) Prior Publication Data

US 2015/0060727 A1   Mar. 5, 2015

Related U.S. Application Data

(62) Division of application No. 13/158,958, filed on Jun. 13, 2011, now Pat. No. 8,884,038.

(51) Int. Cl.

| | |
|---|---|
| *C09K 3/00* | (2006.01) |
| *C09K 15/00* | (2006.01) |
| *C09K 15/06* | (2006.01) |
| *C07C 7/20* | (2006.01) |
| *C08K 5/04* | (2006.01) |
| *C08F 2/40* | (2006.01) |
| *C07C 45/69* | (2006.01) |
| *C07C 45/51* | (2006.01) |
| *C09K 15/08* | (2006.01) |
| *C08K 5/00* | (2006.01) |

(52) U.S. Cl.
CPC ............... *C07C 7/20* (2013.01); *C07C 45/512* (2013.01); *C07C 45/69* (2013.01); *C08F 2/40* (2013.01); *C08K 5/005* (2013.01); *C09K 15/06* (2013.01); *C09K 15/08* (2013.01)

(58) Field of Classification Search
None
See application file for complete search history.

(56) References Cited

U.S. PATENT DOCUMENTS

| | | | | |
|---|---|---|---|---|
| 4,003,800 | A | * | 1/1977 | Bacha et al. ........................ 203/9 |
| 5,583,247 | A | * | 12/1996 | Nesvadba et al. ................. 560/2 |
| 5,670,692 | A | | 9/1997 | Nesvadba et al. |
| 5,750,765 | A | * | 5/1998 | Nesvadba et al. ............ 560/126 |
| 6,046,220 | A | | 4/2000 | Bernardon |
| 7,651,635 | B1 | * | 1/2010 | Lewis ........................... 252/403 |
| 2005/0113625 | A1 | * | 5/2005 | Benage et al. ................. 585/950 |
| 2009/0114878 | A1 | * | 5/2009 | Weyler et al. ........... 252/182.29 |

FOREIGN PATENT DOCUMENTS

WO   9733856 A1   9/1997

* cited by examiner

*Primary Examiner* — Tanisha Diggs
(74) *Attorney, Agent, or Firm* — Eric D. Babych; Brinks Gilson & Lione

(57) ABSTRACT

A method for retarding polymerization of vinyl monomers comprising adding a quinone methide to a liquid comprising the vinyl monomers is described.

4 Claims, No Drawings

7-ACETYLENO QUINONE METHIDE DERIVATIVES AND THEIR APPLICATION AS VINYLIC POLYMERIZATION RETARDERS

CROSS-REFERENCE TO RELATED APPLICATIONS

This application is a divisional application of claiming priority from U.S. patent application Ser. No. 13/158,958 filed on Jun. 13, 2011, now U.S. Pat. No. 8,884,038.

STATEMENT REGARDING FEDERALLY SPONSORED RESEARCH OR DEVELOPMENT

Not Applicable.

BACKGROUND OF THE INVENTION

This invention relates to the process and methods of synthesizing 7-acetylenic quinone methides and using said quinone methides to inhibit and retard polymerization of vinylic monomers. As described in U.S. Pat. No. 7,651,635 quinone methides are used to inhibit the polymerization of vinyl aromatic monomers. These monomers undesirably polymerize at various stages of their manufacture, processing, handling, storage, and use. Vinyl aromatic monomers undergo self-initiated polymerization at elevated temperatures even in the absence of polymerization promoters. Thus, undesired thermal polymerization is particularly problematic especially during the purification process of vinyl aromatic monomers and during emergency shutdown conditions. Undesirable polymerization results in product loss because the valuable monomer end product is consumed. Moreover, polymerization reduces production efficiency as polymer gets deposited on process equipment. This fouling of process equipment may require shutting down so the undesired polymer can be physically removed.

To minimize the problem of unwanted polymerization, two categories of compounds have been developed, namely, inhibitors and retarders. Inhibitors effectively prevent polymerization while the monomer purification process is running uninterrupted. As long as the process is continuously running, the inhibitors are continuously injected into the purification tower along with the feed stream. Conversely, when the process is static, inhibitors cannot be added into the purification tower so that said inhibitors are consumed rapidly. In cases of emergency shutdowns when more inhibitor cannot be added, previously added inhibitor will be rapidly consumed and depleted. Without inhibitors, the unwanted polymerization accelerates rapidly thereby causing fouling of equipment, undesirable consumption of the end product monomer and posing a high safety risk due to runaway exothermic polymerization reactions. Although not as effective as inhibitors, retarders slow polymerization rates. During emergency shutdown conditions, retarders are usually not consumed as quickly so they keep the amount of polymer formed low. As a result, a retarder is more reliable than an inhibitor during emergency shutdown conditions.

At first, only retarders such as sulfur, sulfur dioxide, and dinitrophenols (DNP) (including 2,6-dinitrophenol, 2,4-dinitrocresol, and 2-sec-butyl-4,6-dinitrophenol (DNBP)) were used to prevent unwanted polymerization reactions. Later two classes of inhibitors, viz.; dialkylhydroxylamines (including hydroxypropylhydroxylamine (HPHA)) and stable nitroxides free radicals, were used. To get the most out of both inhibitors and retarders, and because of safety concerns in the event of a plant malfunction, inhibitors are often combined with retarders.

Despite their efficacy and low cost, DNP retarders are highly toxic. Another equally significant disadvantage is that these compounds release $NO_X$ emissions during incineration. So, there is an urgent need for a replacement for these retarders. A class of compounds less toxic and environmentally more benign substitute retarders for DNP comprises quinone methides. Quinone methides slow the rate of polymer formation under static conditions and do not need to be replenished unlike inhibitors. Quinone methide retarders are not very economical unless they are used in combination with inhibitors.

Examples of quinone methide compounds are in U.S. Pat. No. 4,003,800. These 7-alkyl quinone methide compounds, however, are not stable enough for sustained use in industrial settings especially in the case of emergency shutdown. Stable quinone methides are more desirable. Other applications of quinone methides are found in U.S. Pat. Nos. 5,583,247, and 7,045,647. Previous examples of inhibitor-retarder combinations that use DNP are disclosed in U.S. Pat. Nos. 5,446,220 and 6,024,894. These combinations were found to be more effective than DNP alone.

As taught in U.S. Pat. Nos. 5,750,765, 5,670,692, 6,926,820 and 7,651,635 some quinone methides have proven effective and are a "green" non-toxic inhibitor-retarder combination for use in preventing the premature polymerization of styrene and other vinyl aromatic monomers. US Published Patent Application 2009/0287013 discusses the synthesis of one such quinone methide, a manufacturing method that involves the use of highly toxic cyanide that has to be handled with great care. Therefore there is a clear utility and novelty in effective methods of synthesizing other efficient quinone methides. Equally as important, there is a need for retarders that are as efficient as DNBP but as safe as prior art quinone methide compounds.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists. Any and all patents, patent applications, and other references cited by this application are hereby incorporated by reference in their entirety.

BRIEF SUMMARY OF THE INVENTION

At least one embodiment of the invention is directed towards a method for the synthesis of 7-Acetyleno quinone methides. The method comprises the steps of: a) performing a condensation reaction between a 3,5-di-substituted-4-hydroxybenzaldehyde and a secondary amine thereby forming a secondary amine quinone methide intermediate; b) removing water from the secondary amine quinone methide intermediate in a high boiling point aliphatic and also aromatic hydrocarbon solvent by azeotropic distillation at a temperature of between 100 and 160° C.; c) adding the dehydrated secondary amine quinone methide intermediate to an organic medium containing a metal acetylide to form a Mannich base intermediate, and d) adding a release agent to the Mannich base intermediate to yield a 7-Acetyleno quinone methide.

The 3,5-di-substituted-4-hydroxybenzaldehyde may have the formula:

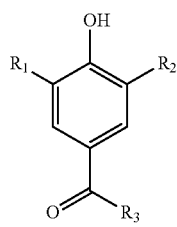

where $R_1$ and $R_2$ are independently selected from $C_4$-$C_{18}$ alkyl, $C_5$-$C_{12}$ cycloalkyl, phenyl and $C_7$-$C_{15}$ phenylalkyl. Preferably, $R_1$ and $R_2$ are tert-butyl, tert-amyl, tert-octyl, cyclohexyl, α-methylbenzyl or α,α-dimethylbenzyl, with tert-butyl, tert-amyl or tert-octyl most preferred. $R_3$ is H.

The secondary amine may be an N,N-disubstitutedamino group, and more specifically a 5-membered heterocyclic group and also a 6-membered heterocyclic group with the structures:

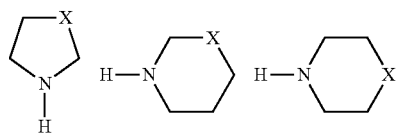

Where X is $CH_2$, O, S, $NR_4$, whereby $R_4$ is selected from $C_1$-$C_{18}$ alkyl, $C_5$-$C_{12}$ cycloalkyl, phenyl and $C_7$-$C_{15}$ phenylalkyl. More preferably, the heterocyclic secondary amine group in claim 1 is an amine in which X is $CH_2$ and O. Most preferably X is $CH_2$.

The secondary amine quinone methide intermediate may be a 4-((N,N-disubstitutedamino)methylene)cyclohexa-2,5-dienone quinone methide molecule with the formula:

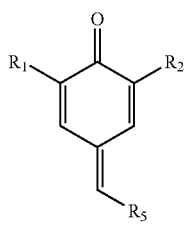

where $R_1$ and $R_2$ are independently selected from $C_4$-$C_{18}$ alkyl, $C_5$-$C_{12}$ cycloalkyl, phenyl and $C_7$-$C_{15}$ phenylalkyl. Preferably, $R_1$ and $R_2$ are tert-butyl, tert-amyl, tert-octyl, cyclohexyl, α-methylbenzyl or α,α-dimethylbenzyl. Most preferably $R_1$ and $R_2$ are tert-butyl, tert-amyl or tert-octyl.

The 4-((N,N-disubstitutedamino)methylene)cyclohexa-2,5-dienone may have $R_5$ being an N,N-disubstitutedamino group, and more specifically 5-membered and 6-membered heterocyclic groups with the structures:

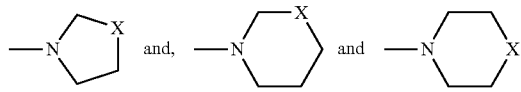

Where X is $CH_2$, O, S, $NR_4$, whereby $R_4$ is selected from $C_1$-$C_{18}$ alkyl, $C_5$-$C_{12}$ cycloalkyl, phenyl and $C_7$-$C_{15}$ phenylalkyl. More preferably, $R_5$ in claim 4 is a 5-membered heterocyclic group and also a 6-membered heterocyclic group in which X is $CH_2$ and O. Most preferably X is $CH_2$.

The Mannich base intermediate may have the molecular formula:

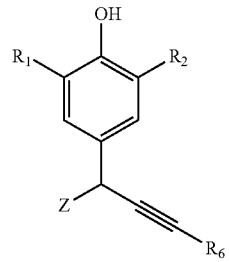

where $R_1$ and $R_2$ are independently selected from $C_4$-$C_{18}$ alkyl, $C_5$-$C_{12}$ cycloalkyl, phenyl and $C_7$-$C_{15}$ phenylalkyl. In at least one embodiment $R_1$ and $R_2$ are tert-butyl, tert-amyl, tert-octyl, cyclohexyl, α-methylbenzyl or α,α-dimethylbenzyl, with tert-butyl, tert-amyl or tert-octyl most preferred. In at least one embodiment $R_6$ is H, $C_1$-$C_{18}$ alkyl, $C_5$-$C_{12}$ cycloalkyl, phenyl, $C_7$-$C_{15}$ phenylalkyl and substituted phenyl group -Ph-$R_7$. Preferably $R_7$ is —COOH, and —COO$R_8$ in which $R_8$ is independently selected from $C_1$-$C_{18}$ alkyl, $C_5$-$C_{12}$ cycloalkyl, phenyl and $C_7$-$C_{15}$ phenylalkyl. Z may be a secondary N,N-disubstitutedamino group, and more specifically may be a 5-membered and 6-membered heterocyclic groups with the structures:

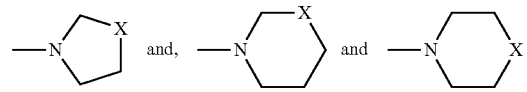

X may be $CH_2$, O, S, $NR_4$, and $R_4$ is selected from $C_1$-$C_{18}$ alkyl, $C_5$-$C_{12}$ cycloalkyl, phenyl and $C_7$-$C_{15}$ phenylalkyl, and any combination thereof. Z may be a 5-membered heterocyclic group and/or a 6-membered heterocyclic group in which X is $CH_2$ and O. More preferably X is $CH_2$. The release agent may be an acid. More preferably the releasing agent is p-toluene sulfonic acid.

At least one embodiment of the invention is directed towards a method for retarding the polymerization of vinyl monomers in a liquid comprising said monomers and a quinone methide compound with the formula:

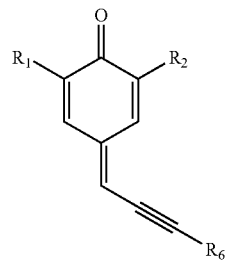

where $R_1$ and $R_2$ are independently selected from $C_4$-$C_{18}$ alkyl, $C_5$-$C_{12}$ cycloalkyl, phenyl and $C_7$-$C_{15}$ phenylalkyl. More preferably, $R_1$ and $R_2$ are tert-butyl, tert-amyl, tert-octyl, cyclohexyl, α-methylbenzyl or α,α-dimethylbenzyl, with tert-butyl, tert-amyl or tert-octyl most preferred. $R_6$ may be H, $C_1$-$C_{18}$ alkyl, $C_5$-$C_{12}$ cycloalkyl, phenyl, $C_7$-$C_{15}$ phenylalkyl and substituted phenyl group -Ph-$R_7$, where Ph is a phenyl group —$C_6H_4$. $R_7$ is —COOH and —COOR$_8$ in which $R_8$ is independently selected from $C_1$-$C_{18}$ alkyl, $C_5$-$C_{12}$ cycloalkyl, phenyl and $C_7$-$C_{15}$ phenylalkyl. The amount of quinone methide added to the monomer may vary from 1 to 10,000 parts per million of said monomer.

DETAILED DESCRIPTION OF THE INVENTION

For purposes of this application the definition of these terms is as follows:

"3,5-di-substituted-4-hydroxybenzaldehyde" means a molecule according to the formula:

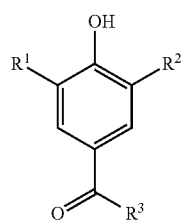

where $R_1$ and $R_2$ are independently selected from $C_4$-$C_{18}$ alkyl, $C_5$-$C_{12}$ cycloalkyl, phenyl and $C_7$-$C_{15}$ phenylalkyl and; Preferably, $R_1$ and $R_2$ are tert-butyl, tert-amyl, tert-octyl, cyclohexyl, α-methylbenzyl or α,α-dimethylbenzyl; with tert-butyl, tert-amyl or tert-octyl most preferred. $R_3$ is H.

"7-Acetyleno Quinone Methide" means a molecule according to the formula:

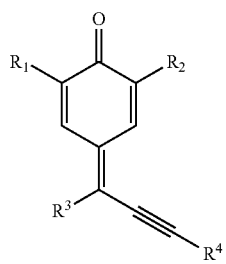

where $R_1$ and $R_2$, are independently selected from $C_4$-$C_{18}$ alkyl, $C_5$-$C_{12}$ cycloalkyl, phenyl and $C_7$-$C_{15}$ phenylalkyl and; Preferably, $R_1$ and $R_2$ are tert-butyl, tert-amyl, tert-octyl, cyclohexyl, α-methylbenzyl or α,α-dimethylbenzyl; with tert-butyl, tert-amyl or tert-octyl most preferred. $R_3$ is independently selected from H, $C_1$-$C_{18}$ alkyl, $C_5$-$C_{12}$ cycloalkyl, phenyl and $C_7$-$C_{15}$ phenylalkyl; most preferably $R_3$ is H, $R_4$ is H, $C_1$-$C_{18}$ alkyl, $C_5$-$C_{12}$ cycloalkyl, phenyl, $C_7$-$C_{15}$ phenylalkyl and substituted phenyl group -Ph-$R_5$, where Ph is a phenyl group —$C_6H_4$, and; $R_5$ is —COOH, and —COOR$_6$ in which $R_6$ is independently selected from $C_1$-$C_{18}$ alkyl, $C_5$-$C_{12}$ cycloalkyl, phenyl and $C_7$-$C_{15}$ phenylalkyl.

"Intermediate 4-((disubstitutedamino)methylene)cyclohexa-2,5-dienone quinone methide" means a molecule with the following structural formula:

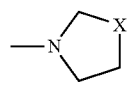

where $R_1$ and $R_2$ are independently selected from $C_4$-$C_{18}$ alkyl, $C_5$-$C_{12}$ cycloalkyl, phenyl and $C_7$-$C_{15}$ phenylalkyl and; Preferably, $R_1$ and $R_2$ are tert-butyl, tert-amyl, tert-octyl, cyclohexyl, α-methylbenzyl or α,α-dimethylbenzyl; with tert-butyl, tert-amyl or tert-octyl most preferred, $R_3$ is a dialkylamino group with the following structure;

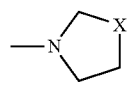

In which $R_6$ and $R_7$ are independently selected from, $C_1$-$C_{18}$ alkyl, $C_5$-$C_{12}$ cycloalkyl, phenyl and $C_7$-$C_{15}$ phenylalkyl; and/or $R_3$ can also be a 5-membered heterocyclic group with the following structure;

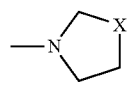

Furthermore, $R_3$ can also be a 6-membered heterocyclic group with the following structure:

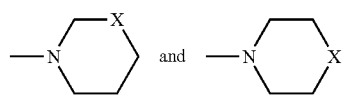

Where X is $CH_2$, O, S, $NR_8$, whereby $R_8$ is selected from $C_1$-$C_{18}$ alkyl, $C_5$-$C_{12}$ cycloalkyl, phenyl and $C_7$-$C_{15}$ phenylalkyl, more preferably, $R_3$ is a 5-membered or 6-membered heterocyclic group in which X is $CH_2$ and O. Most preferably X is $CH_2$. Preferably, $R_3$ is a 6-membered heterocyclic group i.e. piperidinyl. $R_4$ is independently selected from H, $C_1$-$C_{18}$ alkyl, $C_5$-$C_{12}$ cycloalkyl, phenyl and $C_7$-$C_{15}$ phenylalkyl; most preferably $R_4$ is H, preferably the intermediate 4-((disubstitutedamino)methylene)cyclohexa-2,5-dienone is 7-piperidinyl quinone methide derivative.

"7-Piperidinyl quinone methide" means a molecule according to the formula:

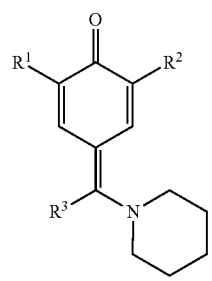

where $R_1$ and $R_2$ are independently selected from $C_4$-$C_{18}$ alkyl, $C_5$-$C_{12}$ cycloalkyl, phenyl and $C_7$-$C_{15}$ phenylalkyl and; Preferably, $R_1$ and $R_2$ are tert-butyl, tert-amyl, tert-octyl, cyclohexyl, α-methylbenzyl or α,α-dimethylbenzyl; with tert-butyl, tert-amyl or tert-octyl most preferred. $R_3$ is independently selected from H, $C_1$-$C_{18}$ alkyl, $C_5$-$C_{12}$ cycloalkyl, phenyl and $C_7$-$C_{15}$ phenylalkyl; most preferably $R_3$ is H.

"Alkoxy" means an alkyl group, as defined herein, attached to the parent molecular moiety through an oxygen atom. Representative alkoxy groups include methoxy, ethoxy, propoxy, butoxy, and the like.

"Alkyl" means a monovalent group derived from a straight or branched chain saturated hydrocarbon by the removal of a single hydrogen atom. Representative alkyl groups include methyl, ethyl, n- and iso-propyl, n-, sec-, iso- and tert-butyl, n-octyl, and the like.

"Cycloalkyl" means a group derived from a monocyclic or bicyclic saturated carbocyclic ring compound by the removal of a single hydrogen atom. Representative cycloalkyl include cyclopropyl, cyclobutyl, cyclopentyl, cyclohexyl, bicyclo[2.2.1]heptanyl, bicyclo[2.2.2]octanyl, and the like.

"Induction time" means the period of time in which in an ideal closed system a composition of matter sufficiently prevents the formation of a particular polymer during a given reaction.

"Inhibitor" means a composition of matter that inhibits the formation of the particular polymer during an induction time but also after the induction time has lapsed, the particular polymer's formation occurs at substantially the same rate that it would form in the absence of the composition of matter.

"Mannich base intermediate" means the Mannich reaction product formed from suitably reacting a metal acetylide salt with the preferred 7-piperidinyl quinone methide intermediate, with the Mannich base intermediate having a molecular formula of:

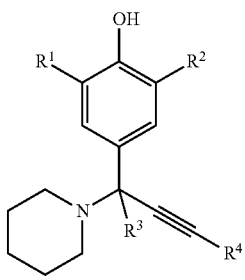

where $R_1$, and $R_2$ are independently selected from $C_4$-$C_{18}$ alkyl, $C_5$-$C_{12}$ cycloalkyl, phenyl and $C_7$-$C_{15}$ phenylalkyl and; Preferably, $R_1$ and $R_2$ are tert-butyl, tert-amyl, tert-octyl, cyclohexyl, α-methylbenzyl or α,α-dimethylbenzyl; with tert-butyl, tert-amyl or tert-octyl most preferred and; $R_3$ is independently selected from H, $C_1$-$C_{18}$ alkyl, $C_5$-$C_{12}$ cycloalkyl, phenyl and $C_7$-$C_{15}$ phenylalkyl. Preferably, $R_3$ is H and; $R_4$ is H, $C_1$-$C_{18}$ alkyl, $C_5$-$C_{12}$ cycloalkyl, phenyl, $C_7$-$C_{15}$ phenylalkyl and substituted phenyl group -Ph-$R_5$ and; $R_5$ is —COOH, and —COOR$_6$ in which $R_6$ is independently selected from $C_1$-$C_{18}$ alkyl, $C_5$-$C_{12}$ cycloalkyl, phenyl and $C_7$-$C_{15}$ phenylalkyl.

"Phenyl" means an aromatic, carbocyclic group of formula $C_6H_5$ where one or more of the H atoms may be replaced with a $C_1$-$C_4$ alkyl, $C_1$-$C_4$ alkoxy, halogen or $C_1$-$C_4$ haloalkyl group.

"Phenylalkyl" means a phenyl group as defined herein, attached to the parent molecular moiety through an alkylene group. Representative phenylalkyl groups include phenylmethyl, phenylethyl, phenylpropyl, and the like.

"Release Agent" means a chemical composition that furnishes the 7-acetyleno quinone methide upon contacting the Mannich base.

"Retarder" means a composition of matter, which does not have an induction time, but instead once added to the given reaction the composition of matter reduces the polymerization rate relative to the rate at which undesirable polymer would have formed in the absence of the composition of matter.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims.

In at least one embodiment a 7-Acetyleno Quinone Methide is synthesized according to the following method. A substituted 4-hydroxybenzaldehyde (such as for example 3,5-di-tert-butyl-4-hydroxybenzaldehyde) undergoes a condensation reaction with a secondary amine (such as for example piperidine), as taught in U.S. Pat. Nos. 5,670,692 and 5,750,765. The condensation reaction results in a secondary amine quinone methide intermediate such as 7-piperidinyl quinone methide. Water is removed (azeotropically or otherwise) from the secondary amine quinone methide intermediate and the intermediate is then added to an organic medium containing a metal acetylide followed by an aqueous acidic workup. This converts the secondary amine quinone methide intermediate into a Mannich base intermediate. A release agent is added to the Mannich base intermediate which yields 7-Acetyleno Quinone Methide.

The use of Mannich base intermediates of Quinone Methides was mentioned in U.S. Pat. Nos. 5,670,692 and 5,750,765. In this case, however the Mannich base intermediate is reacted with highly toxic acetone cyanohydrin during the synthesis of 7-cyano quinine methide. Said method involves the dehydration of 3,5-di-tert-butyl-4-hydroxybenzaldehyde prior to the addition of the secondary amine. In at least one embodiment, the invention excludes this dehydration step.

In at least one embodiment the condensation reaction occurs in the presence an alkane solvent, preferably n-heptane. In at least one embodiment the organic medium is an aromatic solvent preferably toluene, ethylbenzene or xylenes. In at least one embodiment the secondary amine quinone methide intermediate is added to an equimolar amount of metal acetylide. In at least one embodiment the release agent is p-toluenesulfonic acid. In at least one embodiment the release agent is within toluene solvent. In at least one embodiment at least one of the steps are conducted at a temperature of between 100 and 160° C.

In at least one embodiment the 7-Acetyleno quinone methide functions as a retarder during shutdown conditions. In at least one embodiment the 7-Acetyleno quinone methide functions as an inhibitor during continuous monomer distillation. In at least one embodiment this inhibitor inhibits the polymerization of vinyl aromatic monomers such as styrene monomers. In at least one embodiment this inhibitor inhibits the polymerization of vinyl aromatic monomers for example styrene monomers during distillation.

While the invention is not the only method of synthesizing 7-Acetyleno quinone methide, it is far superior to the prior art methods. Prior art methods described in U.S. Pat. No. 6,046,220 are more complex and more expensive synthesis methods. The methods involve the use of 2-trimethylsilylethoxymethyl chloride as a protection agent for the hydroxyl group of 3,5-di-tert-butyl-4-hydroxybenzaldehyde. The protecting agent 2-trimethylsilyethoxymethyl chloride is very expensive. In a subsequent step, a nucleophile lithium trimethylsilylacetylide is produced by contacting trimethylsilylacetylene with n-butyllithium. The reagent n-butyllithium requires careful handling because it is explosive if exposed to moisture, carbon dioxide or oxygen. Thus, the reaction has to be carried out at −78° C. In another further step, the release agent trifluoroacetic acid has to be contacted with the penultimate product at −78° C. to yield the final product.

While U.S. Pat. Nos. 5,750,765, 5,670,692, 6,926,820 and 7,651,635 describe the use of quinone methides as retarders, they do not describe the use of 7-Acetyleno quinone methide compounds. Moreover, they do not predict the unexpectedly superior effects of these quinone methides when compared to other quinone methides.

For illustrative purpose, an example of the production of a prototype of 7-acetylenic quinone methide compounds according to the invention, as well as the determination of the retarding efficacy of the prototype will now be given by way of example and with no limitation.

The foregoing may be better understood by reference to the following examples, which are presented for purposes of illustration and are not intended to limit the scope of the invention.

EXAMPLE 1

Synthesis of 2,6-di-tert-butyl-4-(3-phenylprop-2-ynylidene)cyclohexa-2,5-dienone (7-Phenylacetyleno Quinone Methide (7-Phace-QM))

(a) 2,6-di-tert-butyl-4-(piperidin-1-ylmethylene)cyclohexa-2,5-dienone

Into a 500 mL three-necked round-bottomed flask equipped with a Dean-Stark trap, a condenser, a magnetic stifling bar and a stopper, the following reagents were added; 24.3 g (100 mmoles) of 3,5-di-tert-butyl-4-hydroxybenzaldehyde and 150 mL of n-heptane. The flask was then armed with a dropping funnel charged with 21.7 mL (200 mmoles) of piperidine.

A heating block was used to heat the n-heptane slurry of 3,5-di-tert-butyl-4-hydroxybenzaldehyde at 140° C. The slurry was heated for 30 minutes. To the flask, piperidine was added dropwise. Roughly 2 mL of water, the byproduct of the condensation reaction, was removed by azeotropic distillation using a Dean-Stark trap.

In further experiments, the initial dehydration of 3,5-di-tert-butyl-4-hydroxybenzaldehyde before the addition of piperidine was omitted. Instead, piperidine was added to the flask as soon as the temperature of the heating bath reached 140° C.

Within 30 minutes after the complete addition of piperidine, the release of water stopped and the reaction mixture turned deep olive-green. The hot solution was carefully transferred into a beaker and left to cool down. Crystals were formed as the solution cooled down. Vacuum filtration was used to recover the olive-green 2,6-di-tert-butyl-4-(piperidin-1-ylmethylene)cyclohexa-2,5-dienone solid product. To remove the excess piperidine, the product was washed twice with n-heptane then placed in a three-necked round-bottomed flask for immediate use.

(b) 2,6-di-tert-butyl-4-(3-phenyl-1-(piperidin-1-yl)prop-2-ynyl)phenol)

Sodium phenylacetylide was prepared as follows; a 1-L three-necked flask armed with a condenser, a stopper, and a magnetic stirrer was charged with 13.5 mL (120 mmoles) of phenylacetylene and 100 mL of toluene. Freshly cut sodium metal chips were added to the flask and the contents were heated at 140° C. under reflux. A heating block was used. A beige-colored slurry was formed once all the sodium was consumed. In an alternative method, ethyl magnesium bromide, a Grignard reagent, was used in lieu of sodium metal. In yet another method, sodium hydride was used. The slurry was cooled to 25° C.

To the flask containing the toluene slurry of freshly prepared 2,6-di-tert-butyl-4-(piperidin-1-ylmethylene)cyclohexa-2,5-dienone, the sodium phenylacetylide slurry was transferred while vigorously stirring the contents of the flask. A slight effervescence was observed and, within ten minutes, a wine-red solution was formed. The reaction mixture was heated at 120° C. under reflux. After heating the mixture for 30 minutes, the solution was transferred into a beaker containing a mixture of water and crushed ice. The contents were transferred into a separatory funnel. The aqueous layer was drained off and the Mannich base, 2,6-di-tert-butyl-4-(3-phenyl-1-(piperidin-1-yl)prop-2-ynyl)phenol recovered in the organic phase.

(c) 2,6-di-tert-butyl-4-(3-phenylprop-2-ynylidene)cyclohexa-2,5-dienone (7-Phace-QM)

The organic layer containing the Mannich base 2,6-di-tert-butyl-4-(3-phenyl-1-(piperidin-1-yl)prop-2-ynyl)phenol was transferred into a 1-L three-necked flask equipped with a stopper, a magnetic stifling bar, a dropping funnel and a condenser. The flask was placed on a heating block. The contents were refluxed at 120° C. while an aqueous solution of 20.2 g (107 mmoles) of p-toluene sulfonic acid was added dropwise. After an hour, the p-toluene sulfonic acid addition was complete. The reaction mixture was cooled to room temperature.

A separatory funnel was used to recover the organic layer. The aqueous layer was washed with toluene and the organic layers combined. To the recovered organic layer, anhydrous magnesium sulfate was added followed by filtration. The filtrate was collected and the solvent removed in vacuo. 7-Phace-QM was recovered as a brown solid.

A solution of the 7-Phace-QM product was submitted for GC-MS analysis. On the mass spectrum, there was a parent ion with a m/z ratio of 318, which is in conformity with the molecular weight of 2,6-di-tert-butyl-4-(3-phenylprop-2- ynylidene)cyclohexa-2,5-dienone, the 7-Phace-QM, the acetylenic quinone methide prototype.

(d) A One-Pot Synthesis of 2,6-di-tert-butyl-4-(3-phenylprop-2-ynylidene)cyclohexa-2,5-dienone (7-Phace-QM)

A 1-L three-necked round-bottomed flask armed with a Dean-Stark trap, a condenser, a magnetic stifling bar and a stopper, 24.3 g (100 mmoles) of 3,5-di-tert-butyl-4-hydroxybenzaldehyde and 150 mL of n-heptane were added. The flask was then armed with a dropping funnel containing 21.7 mL (200 mmoles) of piperidine.

A heating block was used to heat the n-heptane slurry of 3,5-di-tert-butyl-4-hydroxybenzaldehyde at 140° C. while piperidine was added to the flask in a drop-wise fashion. The slurry was heated for 30 minutes. Roughly 2 mL of water, the byproduct of the condensation reaction, were removed by azeotropic distillation using a Dean-Stark trap. After the removal of the water, 100 mL of n-heptane were distilled off. Toluene (100 mL) was added to the flask. A slurry of sodium phenylacetylide (100 mmoles), prepared according to the procedure in Example 1 (b), was then added to the flask. The mixture was stirred while under reflux until a dark colored suspension was formed.

The temperature was lowered to 120° C. To effect the acidic work step and the piperidine-releasing step consecutively in the same pot, an aqueous solution of 200 mmoles of p-toluenesulfonic acid was added into the flask drop-wise to yield a wine-red solution. The solution was then cooled to 25° C. and transferred into a separatory funnel. The aqueous layer was drained off and the organic solution containing 7-Phace QM recovered.

(e) A One-Pot Synthesis of 2,6-di-tert-butyl-4-(3-phenylprop-2-ynylidene)cyclohexa-2,5-dienone (7-Phace-QM) using Pyrrolidine as Secondary Amine In lieu of piperidine, pyrrolidine was used with 3,5-di-tert-butyl-4-hydroxybenzaldehyde to synthesize the subsequent intermediate 7-pyrrolidinyl quinone methide following the procedure in Example 1 (d). The remainder of the one-pot procedure towards 7-Phace-QM is as detailed in Example 1 (d).

EXAMPLE 2

A comparison of the performances was made between a sample of a prior art retarder, 7-phenyl-quinone methide, and a sample of the inventive retarder, 7-phenylacetyleno-quinone-methide. A sample of each retarder was added at a dosage of 100 ppm relative to monomer weight. Each of the samples of retarders was placed in a continuously stirred tank reactor that simulates the reboiler of a distillation tower prone to polymerization fouling during a shutdown. Each sample was heated to 120° C. and underwent a 0.5-hour residence. The prior art sample resulted in 6429 ppm of unwanted polymer while the inventive retarder only had 4236 ppm of unwanted polymer. This demonstrates that the inventive retarder has a superior performance compared to prior art retarder.

Compared to DNBP, 7-acetylenic quinone methides are known to be less toxic. Not only are the inventive retarders safer but they also belong to a class of compounds with a history of use as oral and subcutinaceous drugs. Against other quinone methides, 7-acetylenic quinone methides require less toxic starting material during the manufacturing process, in addition to the safety as products.

While this invention may be embodied in many different forms, there are shown and described in detail herein specific preferred embodiments of the invention. The present disclosure is an exemplification of the background and principles of the invention and is not intended to limit the invention to the particular embodiments illustrated. All patents, patent applications, scientific papers, and any other referenced materials mentioned anywhere herein, are incorporated by reference in their entirety. Furthermore, the invention encompasses any possible combination of some or all of the various embodiments explicitly described herein and incorporated herein as well as combinations which exclude one, some, or all but one of the various embodiments explicitly described and/or incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of retarding polymerization of vinyl monomers in a liquid comprising adding a quinone methide compound to said liquid comprising the vinyl monomers, wherein the quinone methide has the following formula:

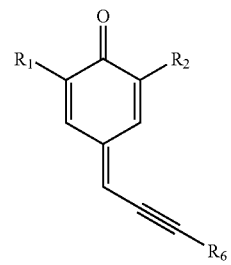

wherein $R_1$ and $R_2$ are independently selected from $C_4$-$C_{18}$ alkyl, $C_5$-$C_{12}$ cycloalkyl, phenyl and $C_7$-$C_{15}$ phenylalkyl and wherein $R_6$ is selected from H, $C_1$-$C_{18}$ alkyl, $C_5$-$C_{12}$ cycloalkyl, phenyl, $C_7$-$C_{15}$ phenylalkyl and a substituted phenyl group-Ph-$R_7$, wherein Ph is a phenyl group —$C_6H_4$ and $R_7$ is —COOH or $COOR_8$ in which $R_8$ is independently selected from $C_1$-$C_{18}$ alkyl, $C_5$-$C_{12}$ cycloalkyl, phenyl and $C_7$-$C_{15}$ phenylalkyl.

2. The method of claim 1 in which the amount of said quinone methide added to the monomer is from 1 to 10,000 parts per million of said monomer.

3. The method of claim 1 wherein $R_1$ and $R_2$ are independently selected from tert-butyl, tert-amyl, tert-octyl, cyclohexyl, α-methylbenzyl and α, α-dimethylbenzyl.

4. The method of claim 1 wherein $R_1$ and $R_2$ are independently selected from tert-butyl, tert-amyl and tert-octyl.

* * * * *